(12) United States Patent
Mahler et al.

(10) Patent No.: US 8,314,273 B2
(45) Date of Patent: Nov. 20, 2012

(54) PRODUCTION PROCESSES FOR MAKING 1,1,1,2,2,3-HEXAFLUOROPROPANE

(75) Inventors: Barry Asher Mahler, Glen Mills, PA (US); Xuehui Sun, Swedesboro, NJ (US); Velliyur Nott Mallikarjuna Rao, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 554 days.

(21) Appl. No.: 12/439,575

(22) PCT Filed: Sep. 4, 2007

(86) PCT No.: PCT/US2007/019349
§ 371 (c)(1),
(2), (4) Date: Oct. 20, 2009

(87) PCT Pub. No.: WO2008/027602
PCT Pub. Date: Mar. 6, 2008

(65) Prior Publication Data
US 2010/0305371 A1    Dec. 2, 2010

Related U.S. Application Data

(60) Provisional application No. 60/842,119, filed on Sep. 1, 2006.

(51) Int. Cl.
*C07C 17/266*    (2006.01)

(52) U.S. Cl. .................................................. 570/172
(58) Field of Classification Search .............. 570/172
See application file for complete search history.

(56) References Cited

U.S. PATENT DOCUMENTS 5,157,171 A    10/1992    Sievert et al.
6,184,426 B1    2/2001    Belen'Kii et al.

FOREIGN PATENT DOCUMENTS

| JP | 06279328 | 10/1994 |
|---|---|---|
| WO | 9008753 A1 | 8/1990 |
| WO | 9008754 A2 | 8/1990 |

OTHER PUBLICATIONS

S. Rudiger et al., Real Sol-Gel Synthesis of Catalytically Active Aluminium Fluoride, J. Sol-gel Sci. Techn., 2007, vol. 41:299-311.
T. Krahl et al., The Very Strong Solid Lewis Acids Aluminium Chlorofluoride (ACF) and Bromofluoride (ABF)-Synthesis, Structure, and Lewis Acidity, Journal of Fluorine Chemistry, 2006, vol. 127:663-678.
G. G. Belen'Kii et al., Electrophilic, Catalytic Alkylation of Polyfluoroolefins by Some Fluoroalkanes, Journal of Fluorine Chemistry, 2001, vol. 108:15-20.

*Primary Examiner* — Jafar Parsa

(57) ABSTRACT

A process for making HFC-236cb is disclosed. The process comprises reacting TFE with HFC-32 in the presence of at least one co-product and a suitable catalyst to produce a product mixture comprising HFC-236cb, wherein the total amount of the at least one co-product is at least 10 ppmv based on the total amount of the tetrafluoroethylene, the difluoromethane and the at least one co-product.

4 Claims, No Drawings

PRODUCTION PROCESSES FOR MAKING 1,1,1,2,2,3-HEXAFLUOROPROPANE

BACKGROUND OF THE INVENTION

1. Field of the Disclosure

The present disclosure relates in general to processes for manufacturing 1,1,1,2,2,3-hexafluoropropane. More particularly, the present disclosure relates to the cost effective and environmentally friendly processes for manufacturing 1,1,1,2,2,3-hexafluoropropane in the presence of a catalyst.

2. Description of Related Art

Halogenated compounds, especially fluorinated compounds, such as fluorocarbons and hydrofluorocarbons, have been widely used in the industry as refrigerants, solvents, cleaning agents, foam blowing agents, aerosol propellants, heat transfer media, dielectrics, fire extinguishing agents, sterilants and power cycle working fluids, et al.

Processes for the production of 1,1,1,2,2,3-hexafluoropropane (HFC-236cb) by using tetrafluoroethylene monomer ($CF_2=CF_2$ or TFE) and difluoromethane ($CH_2F_2$ or HFC-32) as starting materials and using antimony pentafluoride ($SbF_5$) as a catalyst have been described in U.S. Pat. No. 6,184,426.

Current commercially produced TFE is a monomer for use as a starting material in the manufacture of a variety of fluorinated polymer, for example for the manufacture of polytetrafluoroethylene (PTFE)_, among others. The chemistries used in the manufacture of TFE monomer frequently produce a variety of co-products unacceptable in a polymer feedstock, and said TFE monomer manufacturing processes incur significant expense both in equipment and operating costs to remove any such co-products down to low levels to produce high-purity TFE. These purification steps typically increases the production costs of TFE by as much as 5, 10 or even 20%. Such co-products are considered unacceptable in the TFE starting material because of their adverse effect on the properties of the polymer materials produced from the TFE. For example, any number of hydrogen containing fluorocarbons such as pentafluoroethane ($CHF_2CF_3$ or HFC-125) and chlorodifluoromethane ($CHClF_2$ or HCFC-22) are considered objectionable in a TFE product intended for polytetrafluoroethylene (PTFE) manufacture. Carbon dioxide ($CO_2$) is also considered objectionable in a TFE product intended for PTFE manufacture. Residues of such objectionable co-products even as low as 10-100 parts-per-billion by volume (ppbv) are considered unacceptable in such a TFE product.

Similarly, processes that produce HFC-32 typically also produce a variety of co-products that can be expensive both in equipment and operating cost to remove from the final HFC-32 product. For example, the chemistries that produce HFC-32 frequently also include fluorotrichloromethane ($CCl_3F$ or CFC-11), difluorodichloromethane ($CCl_2F_2$ or CFC-12), chlorodifluoromethane ($CHClF_2$ or HCFC-22), and fluoromethane ($CH_3F$ or HFC-41).

The need to remove such co-products from a TFE or HFC-32 product also incurs additional expense in the loss of process materials and the need to provide for environmentally acceptable methods of disposition of such co-product streams. For the 1,1,1,2,2,3-hexafluoropropane from TFE and HFC-32, the additional purification costs of the feed-streams of TFE or HFC-32 can combine to be commercially prohibitive for the intended end use of the 1,1,1,2,2,3-hexafluoropropane, e.g. as an intermediate in the production of refrigeration fluid products. Thus, there is a need for a cost effective and environmentally friendly process for the production of 1,1,1,2,2,3-hexafluoropropane.

SUMMARY OF THE INVENTION

The present disclosure relates to a cost-effective production process for making HFC-236cb from TFE and HFC-32. The process comprises reacting TFE with HFC-32 in the presence of at least one co-product and a suitable catalyst to produce a product mixture comprising HFC-236cb, wherein the total amount of the at least one co-product is at least 10 ppmv based on the total amount of the tetrafluoroethylene, the difluoromethane and the at least one co-product.

The foregoing general description and the following detailed description are exemplary and explanatory only and are not restrictive of the invention, as defined in the appended claims.

DETAILED DESCRIPTION OF THE INVENTION

Before addressing details of embodiments described below, some terms are defined or clarified.

The term "ppmv" is intended to mean parts per million by volume.

The term "perfluorocarbons" is intended to mean chemical compounds composed only of C and F. Perfluorocarbons include both straight and branched compounds. Perfluorocarbons also include both cyclic and acyclic compounds.

The term "perfluoroethers" is intended to mean chemical compounds having ether bonds and composed only of C, O and F. Perfluoroethers include both straight and branched compounds. Perfluoroethers also include both cyclic and acyclic compounds.

The term "perfluoro tertiary amines" is intended to mean tertiary amines wherein all the hydrogens have been substituted by fluorines.

The term "hydrohalocarbons" is intended to mean chemical compounds composing only of H, C and halogens.

The term "co-product" is intended to mean chemical compounds other than TFE generated in a TFE manufacturing process, and chemical compounds other than HFC-32 generated in a HFC-32 manufacturing process. Typically, such co-products include $CO_2$, HCl, fluorotrichloromethane, difluorodichloromethane, chlorodifluoromethane, fluoromethane, among others, The term "a suitable catalyst" is intended to mean a catalyst which can be used to make HFC-236cb. Typical catalysts used to make HFC-236cb include $SbF_5$ and aluminum catalysts. The term "aluminum catalysts" is intended to mean catalysts with the general formula of $AlCl_{3-m}F_m$ or $AlBr_{3-n}F_n$, wherein m is from about 1.0 to 3, and n is from about 2.7 to 3.

In one embodiment of this invention, an aluminum catalyst is $AlF_3$. $AlF_3$ is a known compound, and its preparation method has been disclosed, for example, by S. Rudiger, et al. in J. Sol-Gel Sci. Techn. Volume 41 (2007) 299-311, hereby incorporated by reference in its entirety.

In another embodiment of this invention, an aluminum catalyst is a modified aluminum chloride.

In another embodiment of this invention, an aluminum catalyst is a modified aluminum bromide.

The term "a modified aluminum chloride" is intended to mean an aluminum chlorofluoride containing about 3 to about 64% F by weight.

In one embodiment of this invention, the aluminum chlorofluoride contains about 16 to 61% F by weight. Such aluminum chlorofluoride can be represented by formula $AlCl_{3-x}F_x$ wherein x is typically about 1.0 to about 2.8.

The term "a modified aluminum bromide" is intended to mean an aluminum bromofluoride represented by formula $AlBr_{3-y}F_y$, wherein y is typically about 2.7 to about 2.95.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

A process has been provided for making HFC-236cb. The process comprises reacting TFE with HFC-32 in the presence of at least one co-product and a suitable catalyst to produce a product mixture comprising HFC-236cb, wherein the total amount of said at least one co-product is at least 10 ppmv based on the total amount of said TFE, said HFC-32 and said at least one co-product.

To date, the production methods for HFC-236cb using TFE and HFC-32 have not been considered to be commercially feasible given the expense of the starting materials. The present disclosure thus relates to a more cost effective method of producing HFC-236cb that uses less expensive reactants. These reactants would include many of the coproducts of their individual starting materials, and the production process of HFC-236cb is believed to tolerate these co-products such that their presence would not significantly affect the cost of HFC-236cb manufacture. In addition, it is believed that the presence of at least some of these co-products would provide and increase in stability to the reactants, thereby increasing the safety of plant operations and an additional savings in operating and insurance costs. For example, small amounts of $CO_2$ and HCl acts as stabilizers for TFE, and provide the benefit of making this reactant easier to store and transport. Thus even if the production process were such that the coproducts accumulated and some type of separation system was found to be necessary, such a system would not be required to reduce the coproducts to the ppbv (parts per billion by volume) levels currently used in industry, and thus would be less expensive to operate than those currently in use.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

In one embodiment of the invention, the co-product is selected from the group consisting of the compositions contained in Table 1 below as well as HCl. (The disclosure of these molecules is intended to cover all stereo and structural isomers unless otherwise specified.)

TABLE 1

| Formula | Common Name | Chemical Name |
| --- | --- | --- |
| $CCl_3F$ | CFC-11 | trichlorofluoromethane |
| $CCl_2F_2$ | CFC-12 | dichlorodifluoromethane |
| $CClF_3$ | CFC-13 | chlorotrifluoromethane |
| $CHFCl_2$ | HCFC-21 | dichlorofluoromethane |
| $CHF_2Cl$ | HCFC-22 | chlorodifluoromethane |
| $CHF_3$ | HFC-23 | trifluoromethane |
| $CH_2FCl$ | HCFC-31 | chlorofluoromethane |
| $CH_3F$ | HFC-41 | fluoromethane |
| $C_2Cl_2F_4$ | CFC-114 | dichlorotetrafluoroethane |
| $C_2ClF_5$ | CFC-115 | chloropentafluoroethane |
| $C_2F_6$ | FC-116 | hexafluoroethane |
| $C_2HF_4Cl$ | HCFC-124 | chlorotetrafluoroethane |
| $CHF_2CF_3$ | HFC-125 | pentafluoroethane |
| $CF_3CF_2CF_3$ | FC-218 | octafluoropropane |
| $C_3HCl_2F_5$ | HCFC-225 | dichloropentafluoropropane |
| $C_3HF_6Cl$ | HCFC-226 | chlorohexafluoropropane |
| $C_2Cl_2F_2$ | CFC-1112 | dichlorodifluoroethylene |
| $C_2ClF_3$ | CFC-1113 | chlorotrifluoroethylene |
| $C_2HF_3$ | HFC-1123 | trifluoroethylene |
| $C_2H_2F_2$ | HFC-1132 | difluoroethylene |
| $C_4F_8$ | FC-1318 | octafluoro-2-butene |
| $C_3H_6O$ | Acetone | Acetone |
| $cC_4F_8$ | C318 | octafluorocyclobutane |
| $C_4F_{10}$ | FC-3110 | perfluorobutane |
| CO | CO | carbon monoxide |
| $CO_2$ | $CO_2$ | carbon dioxide |
| $H_2$ | $H_2$ | hydrogen |
| $C_3F_6$ | HFP | hexafluoropropylene |
| $C_4F_6$ | PFBY-2 | Hexafluoro-2-butyne |
| D-Limonene | D-Limonene | D-Limonene |

In another embodiment of the invention, the co-product is selected from the group consisting of $CO_2$ and HCl.

In another embodiment of the invention, TFE fed to the reactor also contains $CO_2$ or HCl, or both. Mixing $CO_2$ or HCl into TFE suppresses the ignitability of the TFE, and provides a safer method of shipping and handling TFE.

In one embodiment of the invention, the total amount of co-product present in the reaction of TFE and HFC-32 is at least 1 ppmv based on the total amount of TFE, HFC-32 and the co-product.

In another embodiment of the invention, the total amount of co-product present in the reaction of TFE and HFC-32 is at least 10 ppmv based on the total amount of TFE, HFC-32 and the co-product.

In another embodiment of the invention, the total amount of co-product present in the reaction of TFE and HFC-32 is at least 100 ppmv based on the total amount of TFE, HFC-32 and the co-product.

In another embodiment of the invention, the total amount of co-product present in the reaction of TFE and HFC-32 is at least 1000 ppmv based on the total amount of TFE, HFC-32 and the co-product.

$SbF_5$ is commercially available from Galaxy Chemicals LLC. (Claremore, Okla., U.S.A.).

Modified aluminum chlorides can be prepared by reacting commercially avaible anhydrous $AlCl_3$ with one or more chlorofluorocarbons, hydrochlorofluorocarbons, or hydrofluorocarbons as disclosed in U.S. Pat. No. 5,157,171 to Sievert, et al., which is incorporated herein by reference. By way of explanation, the modified aluminum chloride catalysts used in the process are prepared by treating anhydrous aluminum chloride with an excess of chlorofluorocarbons, hydrochlorofluorocarbons, or hydrofluorocarbons such as $CH_3F$, $CH_2F_2$, $CHF_3$, $CCl_2FCCl_3$, $CClF_2$, $CCl_3$, $CF_3$, $CCl_3$, $CF_3CCl_2F$, $CF_3CClF_2$, $CHCl_2$ $CCl_2F$, $CHClFCCl_3$, $CHCl_2CClF_2$, $CHClFCCl_2F$, $CHF_2CCl_3$, $CHCl_2CF_3$, $CHClFCClF_2$, $CHF_2CCl_2F$, $CHClFCF_3$, $CHF_2CClF_2$, $C_2HF_5$, $CHClFCHCl_2$, $CH_2ClCCl_2F$, $CH_2FCCl_3$, $CHClFCHClF$, $CHCl_2CHF_2$, $CH_2ClCClF_2$, $CH_2 FCCl_2F$, $CHClFCHF_2$, $CH_2ClCF_3$, $CH_2FCClF_2$, $CHF_2CHF_2$, $CH_2FCF_3$, $CH_2ClCHClF$, $CH_2FCHCl_2$, $CH_3CCl_2F$, $CH_2ClCHF_2$, $CH_2FCHClF$, $CH_3CClF_2$, $CH_2FCHF_2$, $CH_3CF_3$, $CH_2FCH_2Cl$, $CH_3CHClF$, $CH_2FCH_2F$, $CH_3CHF_2$, and $C_2H_5F$; preferably $CCl_2F_2$, $CHCl_2F$, $CHClF_2$, $CH_2ClF$, $CCl_2FCCl_2F$, $CCl_2FCClF_2$, $CClF_2CClF_2$; and most preferably $CCl_3F$. It is believed that propane derivatives displaying the structural features shown above may also be used in the process of this invention. The reaction between aluminum chloride and the chlorofluorocarbons, hydrochlorofluorocarbons, or hydrofluorocarbons occurs, for the most part, spontaneously and is exothermic. In certain instances, such as with $C_2$ chlorofluorocarbons, slight heating may be used advantageously. For compounds containing —$CF_3$ groups such as $CHF_3$, $CCl_3CF_3$, $CHCl_2CF_3$, $CH_2ClCF_3$, and $CH_3CF_3$ more vigorous conditions are required to effect reaction with AlCl3, and the reaction is best carried out under the pressure developed autogenously by the reactants. After the reaction has subsided, the liquid products are removed, generally under reduced pressures to provide a modified aluminum chloride catalyst which will usually contain from about 3 to about 68% fluorine by weight. The liquid product from the reaction of chlorofluorocarbons with $AlCl_3$ includes products which are produced by halogen exchange reaction with the aluminum chloride as well as rearranged chlorofluorocarbons.

The solid modified aluminum chloride product of the reaction of $AlCl_3$ with chlorofluorocarbons may be separated from the liquid products by filtration, by distillation or vacuum transfer of the liquid products from the modified aluminum chloride, or, alternatively, the modified aluminum chloride catalyst may be used as a suspension for subsequent reactions.

Modified aluminum bromides can be prepared by reacting commercially avaible anhydrous $AlBr_3$ with $CCl_3F$ as disclosed in Journal of Fluorine Chemistry 127 (2006) 663-678 by T. Krahl and E. Kemnitz, which is incorporated herein by reference.

In one embodiment of this invention, the modified aluminum chloride catalyst or the modified aluminum bromide catalyst is produced before the catalyst is contacted with TFE or HFC-32.

In another embodiment of this invention, HFC-32 may also be employed in the formation of modified aluminum chloride catalyst. Use of sufficient excess of HFC-32 enables the production of modified aluminum chloride catalyst in situ from anhydrous aluminum chloride so that the catalyst modification reaction need not be carried out as a separate step.

In another embodiment of this invention, HFC-32 may also be employed in the formation of modified aluminum bromide catalyst. Use of sufficient excess of HFC-32 enables the production of modified aluminum bromide catalyst in situ from anhydrous aluminum bromide so that the catalyst modification reaction need not be carried out as a separate step.

In yet another embodiment of this invention, TFE and HFC-32 can be simultaneously contacted with the anhydrous aluminum chloride or the anhydrous aluminum bromide.

The molar ratio of HFC-32 to TFE fed to the reactor is at least 1:1. In one embodiment of this invention, the molar ratio of HFC-32 to TFE fed to the reactor is at least 3:1. In another embodiment of this invention, the molar ratio of HFC-32 to TFE fed to the reactor is at least 5:1

Optionally, solvents may be employed in the reaction process. In one embodiment of the invention, HFC-32 is also used as a solvent. In another embodiment of the invention, the solvent is an inert chemical compound and shall not react with other chemical compounds or catalysts during the reaction. In one embodiment of the invention, a suitable inert solvent may be selected from the group consisting of perfluorocarbons, perfluoroethers, perfluoro tertiary amines and hydrohalocarbons which will not react with other chemical compounds or catalysts during the reaction.

In one embodiment of the invention, the inert solvent is HFC-236cb.

In one embodiment of this invention, when $SbF_5$ is used as the catalyst, HFC-32 and $SbF_5$ are pre-mixed, optionally in the presence of a solvent, before contacting with TFE.

In another embodiment of this invention, when $SbF_5$ is used as the catalyst, no HF is fed independently to the reactor. It is understood that $SbF_5$ and other chemical compounds fed to the reactor, such as HFC-32 and TFE, may contain small amounts of HF impurities. HF may also be generated by the side-reactions, e.g. $SbF_5$ reacting with moistures in solvents or other chemical compounds. However, HF should be generally avoided.

When $SbF_5$ is used as the catalyst, the temperature employed in the reaction process typically ranges from about $-60°$ C. to $-10°$ C. In one embodiment of the invention, the temperature employed in the reaction process ranges from about $-50°$ C. to $-10°$ C. In another embodiment of the invention, the temperature employed in the reaction process ranges from about $-40°$ C. to $-10°$ C. In another embodiment of the invention, the temperature employed in the reaction process ranges from about $-35°$ C. to $-10°$ C.

When $SbF_5$ is used as the catalyst, the reaction time is not critical and typically ranges from about 5 seconds to about 10 hours. In one embodiment of the invention, the reaction time ranges from about 1 hour to about 5 hours.

When $SbF_5$ is used as the catalyst, the pressure employed in the reaction is not critical. Typically, the reaction is conducted under autogenous pressure.

When modified aluminum chloride or modified aluminum bromide is used as the catalyst, the temperature employed in the reaction process typically ranges from about $-10°$ C. to $-200°$ C. In one embodiment of the invention, the temperature employed in the reaction process ranges from about $0°$ C. to $100°$ C.

When modified aluminum chloride or modified aluminum bromide is used as the catalyst, the reaction time is not critical and typically ranges from about 0.25 hours to about 24 hours.

The product HFC-236cb can be recovered from the product mixtures by distillation, e.g. fractional distillation.

The reactors, distillation columns, and their associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

EXAMPLES

The concepts described herein will be further described in the following examples, which do not limit the scope of the invention described in the claims.

Legend:

FC-116 is $CF_3CF_3$
FC-218 is $CF_3CF_2CF_3$
C318 is octafluorocyclobutane
HCFC-31 is $CH_2FCl$
HFC-245cb is $CH_3CF_2CF_3$
HFC-23 is $CHF_3$
HFP is hexafluoropropylene
HCFC-235cb is $CH_2ClCF_2CF_3$

Example 1

Example 1 demonstrates that HFC-236cb can be produced successfully in the presence of $CH_3F$ (HFC-41).

HFC-32 (13 g, 0.25 mol), HFC-41 (8 g, 0.25 mol) and $SbF_5$ (13 g, 0.06 mol) were mixed in a 400 ml shaker tube reactor at −35° C. Then TFE (30 g, 0.3 mol) was fed into the reactor. The mixture was stirred at room temperature for 4 hours. The product (46 g) was then vapor transferred into a 500 ml stainless steel cylinder. The liquid phase of the product was analyzed and the results (GC-TCD area %) are shown in Table 2 below. Small amounts of other by-products having GC area % less than 0.1 are not included in Table 2.

TABLE 2

| HFC-32 | FC-116 | HFC-125 | HFC-236cb | HFC-245cb |
|---|---|---|---|---|
| 23.1 | 0.28 | 23.36 | 7.40 | 45.70 |

Example 2

Example 1 demonstrates that HFC-236cb can be produced successfully in the presence of $CO_2$, FC-116, FC-218, and HFC-125.

A 1000 ml Hastelloy autoclave reactor was charged with $SbF_5$ (64 g, 0.29 mol). The reactor was cooled down to −30° C. and evacuated. The reactor was then charged with HFC-32 (169 g, 3.25 mol) and HFC-236cb (200 g, 1.32 mol). The mixture was stirred and then warmed up to −10° C. Then at −10° C. the HFC-32/TFE/$CO_2$ (1.1:1:0.1 molar ratio) mixture was fed into the reactor at 400 ml/min while the stir continued. The temperature of the reactor was controlled between −12° C. to −9° C. After a total of 260 g of the HFC-32/TFE/$CO_2$ mixture had been added, the feeding was stopped. Then the reaction mixture was stirred at −10° C. for 1 hour. The product mixture was collected in a cold trap. At the end of the reaction, vapor phase of the product mixture in the reactor was analyzed by GC-MS. The analytical results are given in units of GC-MS area % in Table 3 below. The vapor phase sample was taken at −10° C. and 52 psig from vapor space in the reactor. FC-116, HFC-125 and FC-218 were found in the product mixture.

TABLE 3

| HFC-32 | $CO_2$ | HFC-125 | FC-218 | FC-116 | HFC-236cb | Air |
|---|---|---|---|---|---|---|
| 40.97 | 8.32 | 0.116 | 0.093 | 6.27 | 34.95 | 9.2 |

Example 3

Example 3 demonstrates that HFC-236cb can be produced successfully in the presence of HFC-23 and C318.

A 1000 ml Hastelloy autoclave reactor was charged with $SbF_5$ (71 g, 0.33 mol). The reactor was cooled down to −30° C. and evacuated. The reactor was then charged with HFC-32 (164 g, 3.15 mol) and HFC-236cb (200 g, 1.32 mol). The mixture was stirred and then warmed up to −10° C. Then at −10° C. the HFC-32/TFE (1.1:1 molar ratio) mixture was fed into the reactor at 400 ml/min while the stir continued. The temperature of the reactor was controlled between −12° C. to −9° C. After a total of 260 g of the HFC-32/TFE mixture had been added, the feeding was stopped. Then the reaction mixture was stirred at −10° C. for 1 hour. The product mixture was collected in a cold trap. At the end of the reaction, vapor phase of the product mixture in the reactor was analyzed by GC-MS. The analytical results are given in units of GC-MS area % in Table 4 below. The vapor phase sample was taken at −10° C. and 65 psig from vapor space in the reactor. FC-116, HFC-125 and FC-218 were found in the product mixture.

TABLE 4

| HFC-32 | HFC-23 | HFC-125 | FC-218 | FC-116 | HFC-236cb | C318 |
|---|---|---|---|---|---|---|
| 38.35 | 0.336 | 0.061 | 0.068 | 8.72 | 51.56 | 0.021 |

Example 4

Example 4 demonstrates that HFC-236cb can be produced successfully in the presence of HFP.

A 400 ml Hastelloy C shaker tube reactor was charged with 5 g of modified aluminum chloride. The reactor was cooled to −20° C. and evacuated. The reactor was then charged with 23.4 g (0.45 mol) of HFC-32, 30 g (0.3 mol) of TFE and 3 g (0.02 mol) of HFP. Then the reaction mixture was stirred at 60° C. for 6 hours. Product mixture was collected in a cold trap and was analyzed by GC-MS. The analytical results are given in units of GC-MS area % in Table 5 below. Small amounts of other by-products having GC area % less than 0.1 are not included in Table 5.

TABLE 5

| HFC-32 | TFE | FC-116 | HFC-236cb | HFP |
|---|---|---|---|---|
| 6.189 | 8.791 | 0.282 | 62.75 | 11.16 |

Example 5

Example 5 demonstrates that HFC-236cb can be produced successfully with HCFC-31.

A 400 ml Hastelloy C shaker tube reactor was charged with 5 g of modified aluminum chloride. The reactor was cooled to −20° C. and evacuated. The reactor was then charged with 30.8 g (0.45 mol) of HCFC-31 and 30 g (0.3 mol) of TFE. Then the reaction mixture was stirred at room temperature for 6 hours. The liquid phase of the product mixture was analyzed by GC. The analytical results are given in units of GC-TCD area % in Table 6 below. Small amounts of other by-products having GC area % less than 0.1 are not included in Table 6.

TABLE 6

| HFC-32 | TFE | HCFC-235cb | HFC-236cb |
|---|---|---|---|
| 3.117 | 0.413 | 77.64 | 14.44 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for making 1,1,1,2,2,3-hexafluoropropane, comprising: reacting tetrafluoroethylene with difluoromethane in the presence of at least one co-product and a suitable catalyst to produce a product mixture comprising 1,1,1,2,2,3-hexafluoropropane, wherein the total amount of said at least one co-product is at least 10 ppmv based on the total amount of said tetrafluoroethylene, said difluoromethane and said at least one co-product.

2. The process of claim 1 wherein said at least one co-product is selected from the group consisting of $CO_2$, HCl, $CCl_3F$, $CCl_2F_2$, $CClF_3$, $CHFCl_2$, $CHF_2Cl$, $CHF_3$, $CH_2FCl$, $CH_3F$, $C_2Cl_2F_4$, $C_2ClF_5$, $C_2F_6$, $C_2HF_4Cl$, $CHF_2CF_3$, $CF_3CF_2CF_3$, $C_3HCl_2F_5$, $C_3HF_6Cl$, $C_2Cl_2F_2$, $C_2ClF_3$, $C_2HF_3$, $C_2H_2F_2$, $C_4F_8$, $C_3H_6O$, $cC_4F_8$, $C_4F_{10}$, CO, $H_2$, $C_3F_6$, $C_4F_6$, and D-Limonene.

3. The process of claim 1 wherein said at least one co-product is selected from the group consisting of $CO_2$ and HCl.

4. The process of claim 1 wherein said suitable catalyst is selected from the group consisting of $SbF_5$ and aluminum catalysts.

* * * * *